United States Patent [19]

Sahatjian

[11] Patent Number: 5,533,516
[45] Date of Patent: Jul. 9, 1996

[54] SAMPLE COLLECTION

[75] Inventor: Ronald A. Sahatjian, Lexington, Mass.

[73] Assignee: Boston Scientific Corporation, Watertown, Mass.

[21] Appl. No.: 392,101

[22] Filed: Feb. 22, 1995

Related U.S. Application Data

[63] Continuation of Ser. No. 175,949, Dec. 30, 1993, Pat. No. 5,409,012.

[51] Int. Cl.$^6$ .................................................. A61B 10/00
[52] U.S. Cl. ............................................. 128/749; 604/96
[58] Field of Search ................................ 128/749, 752, 128/756, 757; 604/96, 101, 194

[56] References Cited

U.S. PATENT DOCUMENTS

| | | | |
|---|---|---|---|
| 3,577,981 | 5/1971 | Kuris | 128/2 R |
| 3,777,743 | 12/1973 | Binard et al. | 128/2 |
| 3,996,935 | 12/1976 | Banko | 128/276 |
| 4,172,446 | 10/1979 | Bucalo | 128/769 |
| 4,299,226 | 11/1981 | Banka | 128/344 |
| 4,364,392 | 12/1982 | Strother et al. | 128/325 |
| 4,403,612 | 9/1983 | Fogarty | 128/344 |
| 4,423,725 | 1/1984 | Baran et al. | 604/101 |
| 4,623,329 | 11/1986 | Drobish et al. | 604/29 |
| 4,735,214 | 4/1988 | Berman | 128/759 |
| 4,763,670 | 8/1988 | Manzo | 128/756 |
| 4,766,907 | 8/1988 | de Groot et al. | 128/754 |
| 4,820,270 | 4/1989 | Hardcastle et al. | 604/96 |
| 4,832,034 | 5/1989 | Pizziconi et al. | 128/632 |
| 4,875,486 | 10/1989 | Rapoport et al. | 128/653 |
| 4,958,625 | 9/1990 | Bates et al. | 128/754 |
| 4,994,033 | 2/1991 | Shockey et al. | 604/101 |
| 5,006,526 | 4/1991 | Meier et al. | 514/250 |
| 5,026,607 | 6/1991 | Kiezulas | 428/423 |
| 5,049,132 | 9/1991 | Shaffer et al. | 604/101 |
| 5,091,205 | 2/1992 | Fan | 427/2 |
| 5,135,516 | 8/1992 | Sahatjian et al. | 604/265 |
| 5,186,172 | 2/1993 | Fiddian-Green | 128/632 |
| 5,197,470 | 3/1993 | Helfer et al. | 128/634 |
| 5,213,576 | 5/1993 | Abiuso et al. | 604/96 |
| 5,213,577 | 5/1993 | Kratzer | 604/101 |
| 5,217,456 | 6/1993 | Narciso, Jr. | 605/15 |
| 5,238,002 | 8/1993 | Devlin et al. | 128/751 |
| 5,254,089 | 10/1993 | Wang | 604/96 |
| 5,328,470 | 7/1994 | Nabel et al. | 604/101 |
| 5,389,074 | 2/1995 | Parker et al. | 604/96 |

FOREIGN PATENT DOCUMENTS

| | | |
|---|---|---|
| 0399712A1 | 11/1990 | European Pat. Off. . |
| 1069826 | 1/1984 | U.S.S.R. . |
| WO88/06861 | 9/1988 | WIPO . |
| WO92/08515 | 5/1992 | WIPO . |
| WO92/11895 | 7/1992 | WIPO . |
| WO92/07806 | 4/1993 | WIPO . |

OTHER PUBLICATIONS

Nabel et al., "Gene Transfer Into Vascular Cells", 1991, *JACC*, 17(6):189B–194B.

*Primary Examiner*—Max Hindenburg
*Attorney, Agent, or Firm*—Fish & Richardson

[57] ABSTRACT

Taking a bodily sample, e.g., a cell sample, from deep within the body of a patient and collecting the sample outside the body to facilitate treatment of the patient. A sampling probe is provided in the form of an elongate catheter having a proximal portion that remains outside the body and a distal portion that can be located within the body. The distal portion includes a membrane with openings that communicate with space that communicates with a source of suction force. The catheter is positioned within the body. The sample is taken by exposing the membrane by placing it in proximity with a desired location so that the bodily sample is received by the membrane. The catheter is removed from the patient, the sample is collected outside the body, treated, disposed onto a device, such as a graft, stent, or catheter, and reintroduced into the body at a desired site.

18 Claims, 3 Drawing Sheets

SAMPLE COLLECTION

This is a continuation of copending application Ser. No. 08/175,949 filed Dec. 30, 1993, now U.S. Pat. No. 5,409,012.

FIELD OF THE INVENTION

The invention relates to collecting bodily samples from a patient.

BACKGROUND OF THE INVENTION

Samples of tissue, bodily fluids, etc. are frequently taken from patients for analysis to help in diagnosing disease or monitoring the progress of treatment. For example, samples of cells from the lungs or gastrointestinal tract are taken with a cytology brush. The brush is rubbed against tissue to scrape cells from the surface and collect them in the bristles. Other sampling techniques sever tissue from the body. For example, biopsies are taken with a needle device that penetrates the tissue and then severs a sample with a sharp cutting cannula. A biopsy forceps device is another example. This device is a catheter with a jaw-type cutter at its end. The catheter is threaded through an endoscope to a position deep within the body where it bites a sample of tissue from a desired location. Samples of tissue are taken from within blood vessels using an artherectomy cutter. An artherectomy cutter is a catheter that can be threaded through a blood vessel to a desired site. A cutting member is provided at the end of the catheter. The cutting member can be pressed against a desired site in the blood vessel, such as the site of a vascular occlusion resulting from the build up of plaque, and then actuated to sever occluding matter from the wall of the blood vessel. Samples of bodily fluids are typically drawn from body conduits.

SUMMARY OF THE INVENTION

In a first aspect, the invention features a method for taking a bodily sample from a blood vessel of a patient and collecting the sample outside the body to facilitate treatment of the patient. The method includes providing a sampling probe in the form of an elongate vascular catheter having a proximal portion that remains outside the body and a distal portion that can be located in the blood vessel. The distal portion includes an expandable member that can be selectively expanded to larger diameter and contracted to smaller diameter. The expandable member includes a membrane that has openings that communicate with space, that in turn communicates with a source of suction force. The method includes positioning the expandable portion at a desired location within the blood vessel, taking the sample by exposing the membrane by expanding the expandable portion sufficient to place the membrane in proximity with the wall of the blood vessel so that the bodily sample is received by the membrane, contracting the expandable portion to smaller diameter so that the polymer does not contact the wall of the blood vessel, removing the catheter from the patient, and collecting the sample outside the body.

Embodiments may include one or more of the following features. The method includes drawing the sample to the surface of the membrane by suction forces. The method includes drawing the sample through the membrane into the space by the suction forces. The method includes removing the sample from the membrane by a flushing force back out through the openings. The method includes expanding the expandable portion to contact the membrane with the vessel wall. The method includes moving the catheter axially while the membrane is in contact with the wall of the vessel to brush the membrane along the wall. The method includes providing a probe in the form of an angioplasty catheter having an expandable portion in the form of an inflatable balloon, the membrane being disposed on the balloon. The method includes positioning the expandable portion adjacent an occlusion in the vessel, simultaneously expanding the occlusion, and collecting the sample by expanding the expandable portion. The method includes performing angioplasty on an occluded region of the blood vessel, positioning the expandable portion adjacent the region at the region after the angioplasty, and collecting the sample from the region. The method includes taking cells from the body and placing them back into the body.

In another aspect, the invention features a kit for treating a patient by collecting a sample from the blood vessel of a patient that can be analyzed to determine physiological function. The kit includes a sampling probe in the form of an elongate vascular catheter having a proximal portion that remains outside the body and a distal portion that can be located in the blood vessel. The distal portion includes an expandable member that can be selectively expanded to larger diameters and contracted to smaller diameter. The expandable member includes a membrane on at least a part of the expandable member. The membrane includes openings that communicate with a sample storage space that may receive the sample. The storage space communicates with a suction device, controllable from proximal portions outside the body, for creating a suction force through the openings to draw bodily sample into the storage space. Apparatus are provided for facilitating analysis of the sample to determine physiological function.

In another aspect, the invention features taking a bodily sample from deep within the body of a patient and collecting the sample outside the body to facilitate treatment of the patient. A sampling probe is provided in the form of an elongate catheter having a proximal portion that remains outside the body and a distal portion that can be located within the body. The distal portion includes a membrane with openings that communicate with space that communicates with a source of suction force. The catheter is positioned within the body. The sample is taken by exposing the membrane by placing it in proximity with a desired location so that the bodily sample is received by the membrane. The catheter is removed from the patient, and the sample is collected outside the body.

The invention has many advantages. In embodiments, a sample of tissue or bodily fluid containing cells or chemical indicators of biological function can be collected from a site within a blood vessel in a low stress manner. This is an advantage since mechanically disturbing the vessel can cause further injury by inducing intimal proliferation (excessive scar forming) or dislodging portions of the occluding material on the vessel wall so that they enter the bloodstream.

Other features and advantages follow.

BRIEF DESCRIPTION OF THE DRAWING

FIG. 1 is a perspective view of sample collection apparatus; while

FIG. 2 is an enlarged view of the distal end of the apparatus in FIG. 1; while

FIG. 3 and 3a are views similar to FIGS. 2 and 2a, illustrating drawing bodily sample material;

FIG. 4 is a view of the distal end with bodily sample material collected; and

FIG. 5 is a view illustrating removal of the bodily sample from the apparatus outside the body; and FIG. 6 illustrates analyzing the bodily sample material.

DESCRIPTION OF THE PREFERRED EMBODIMENTS

Figure 1:
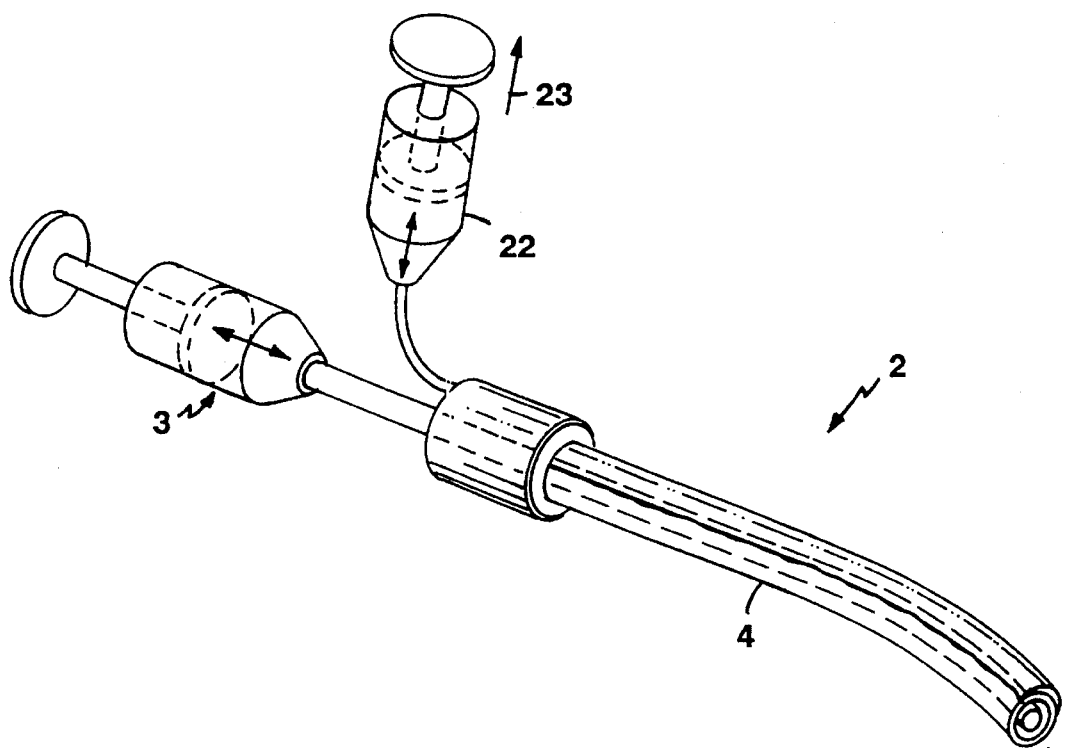
FIGS. 1–6 illustrate the structure and use of an embodiment of the invention.

Referring to FIG. 1, a sample collection apparatus 2 includes a catheter 4 that is constructed to be threaded through a lumen of a blood vessel. The catheter 4 includes near its distal end an expandable portion, which may be, for example, a balloon 8. The balloon is inflated and deflated by injecting or withdrawing fluid from a source 3 through a lumen 5 in the catheter and a port 10 located within the balloon. The apparatus may include a protective sheath 30 that extends over the balloon while it is threaded into and out of the body. The balloon can be exposed from the sheath once the site is reached. The sheath may be an introducer catheter of the type used to direct angioplasty catheters to the coronary arteries.

Figure 1A:
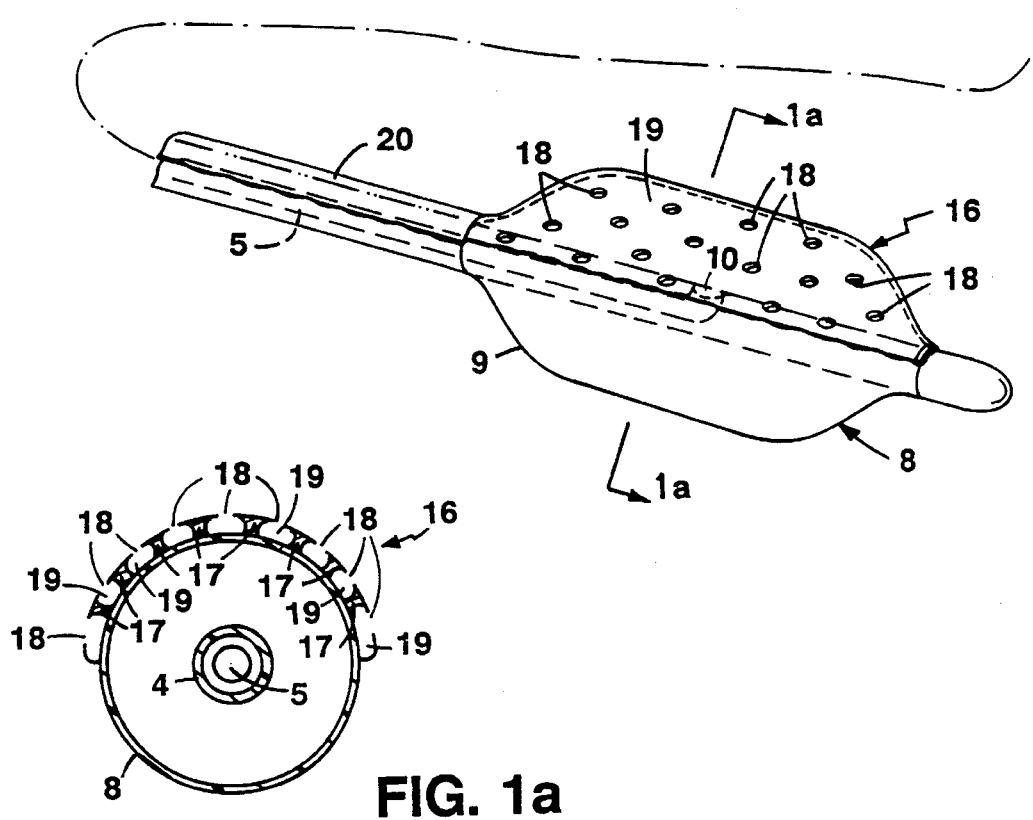
FIG. 1a is a cross-sectional view along the line a—a in FIG. 1.

Referring as well to FIG. 1a, a cross-section along the line aa in FIG. 1, the apparatus also includes a membrane 16 on at least a portion of the outer surface of the balloon 8. The membrane includes a series of openings 18 that communicate with storage space 19 between the outer surface of the balloon and the inner surface of the membrane. The storage space 19 communicates with a lumen 20 that extends through the catheter to a source of suction force, e.g. a syringe 22, at the proximal end of the device. The membrane includes support struts 17 in the storage space to prevent the membrane from collapsing during suction.

Figure 2A:
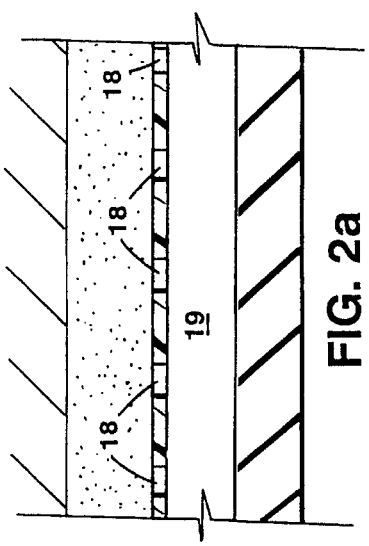
FIG. 2a is a greatly enlarged view of the area in the circle in FIG. 2.
Figure 2:
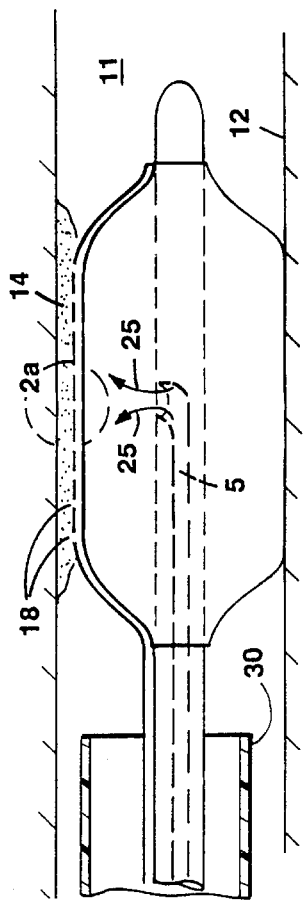

Referring to FIG. 2, an enlarged view of the distal end of the device, the balloon is positioned inside a blood 8 vessel 11 so the membrane 16 is adjacent a portion 14 of the vessel wall 12 that is diseased. For example, the portion 14 may be an occlusion caused by the build-up of plaque or the growth of smooth muscle cells, a condition known as intimal proliferation. The portion of the vessel may have already been treated by balloon catheter angioplasty so that the lumen is substantially open.

Referring as well to FIG. 2a, which is a greatly enlarged view of the area in the circle in FIG. 2, the balloon 8 is inflated by introducing inflation fluid (arrows 25) so that the outer surface of the membrane is in intimate contact with or a short distance from the surface of wall portion 14.

Figure 3A:
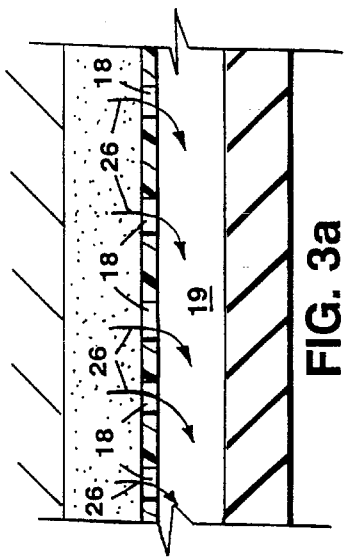
Figure 3:
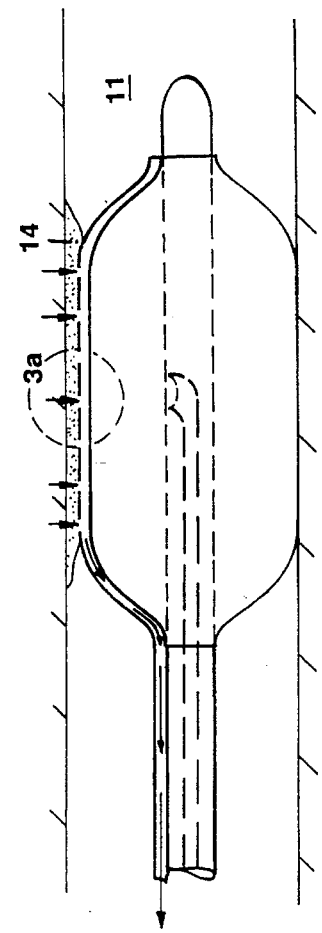

Referring to FIGS. 3 and 3a, a suction force (created by actuating (arrow 23) syringe 22, see FIG. 1) draws bodily sample material from the wall portion 14 through the openings 18 into the storage space 19 (arrows 26).

Figure 4:
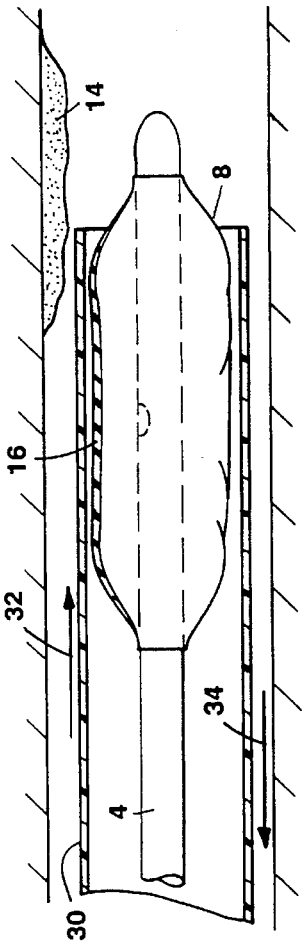

Referring to FIG. 4, with the bodily sample material collected in the space 19, the balloon 8 is deflated to a small size. The protective sheath 30 may be slid axially over the balloon (arrow 32), and the catheter removed from the body (arrow 34). (The sheath may be a guiding catheter into which the sampling catheter is drawn.)

Figure 5:
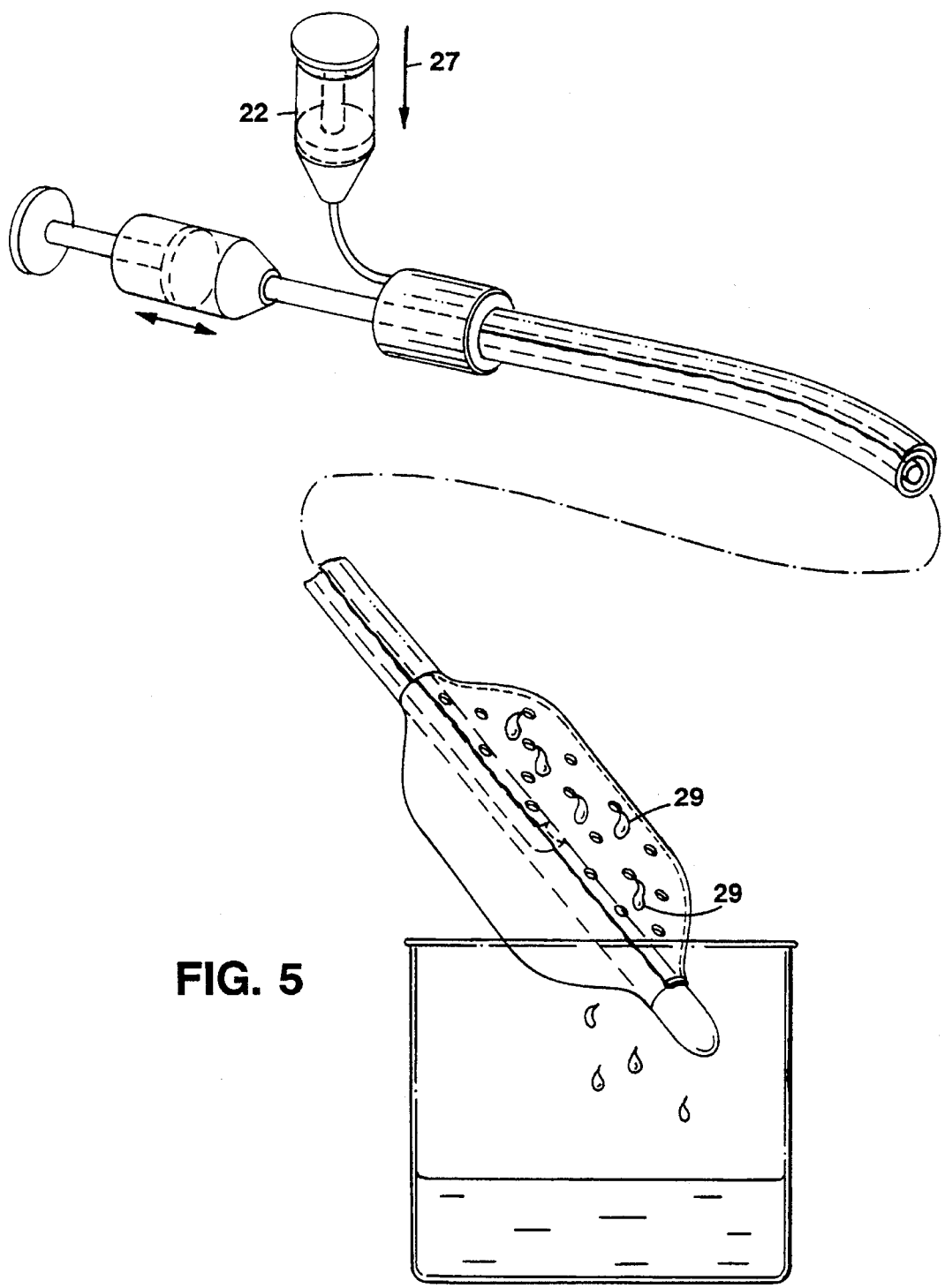
Figure 6:
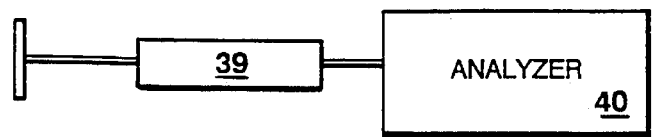

Referring to FIG. 5, outside the body, the bodily sample is removed from the space 19 by actuating the syringe 22 (arrow 27) to flush it from the space 19, back out of the openings 18 (arrow 29), and into a laboratory vessel 38. In other embodiments, the sample can be drawn from the body to the sample space, through the lumen 20, to be collected outside the body while the balloon is still in the body. Referring to FIG. 6, a sample of the bodily material is then placed, e.g., injected with a syringe 39, into an analyzer 40.

An example of a balloon catheter arrangement that can be configured and used as taught here is disclosed in Wang, U.S. Pat. No. 5,254,089, the entire contents of which is hereby incorporated by reference. In that system, the sample space is provided as a series of lumens that are in the walls of the balloon itself. The lumens communicate with openings on the outer surface of the balloon. The lumens in the balloon wall are connected to a manifold that communicates with a lumen extending through the catheter to the proximal end so that suction force can be applied. To prepare the apparatus to take a sample, the lumens are primed before entry into the body, by drawing saline through the openings. Another balloon catheter arrangement is described in U.S. Ser. No. 07/796,402, filed Nov. 22, 1991. In that device a balloon with apertures is positioned over another balloon with space therebetween. The entire contents of this latter case is also incorporated herein by reference.

In embodiments, the characteristics of the membrane can be selected based on the type of bodily sample to be taken. For example, the size of the openings can be selected to collect bodily fluid samples and reject cell samples. In this case, the openings may be about 0.5 to 0.1 micron, which permits fluid to enter but prevents cells from entering. On the other hand, the openings may be selected so that cells may enter. For example, the size of the openings may be about 50 to 75 μm. In some embodiments, in which the openings are too small to allow cells to pass, cell samples may nevertheless be taken in some cases because the cells can become attached to the surface by a wedging effect that occurs when cells are drawn partially into the pores.

The membrane need not cover the entire surface of the balloon. Rather, only a portion, e.g. one half (FIG. 1) or one third of the surface may be covered; the covered surface is then aligned with a corresponding target (e.g. diseased) portion of the vessel wall. The balloon can include several spatially separated membranes with isolated, non-communicating storage spaces. The membranes can be used to take samples from different sites in the vessel in a sequential fashion without removing the catheter from the vessel.

In embodiments, a hydrogel polymer may be provided on the exterior of the membrane to increase lubricity. Suitable polymers are described in Sahatjian et al. U.S. Pat. No. 5,135,516, Fan U.S. Pat. No. 5,091,205 and Sahatjian, "Drug Delivery System", U.S. Pat. No. 5,304,121 filed Nov. 22, 1991. The entire contents of each of these cases is incorporated by reference. A swellable or sponge-like polymer can be provided in the storage space to hold the sample.

Taking samples by suction force is advantageous since it is a gentle removal that effectively sloughs material, e.g. cells, fluid from the surface and does not subject the body to the great trauma associated with severing or abraiding. In other embodiments, samples can be taken in low stress manners in which the membrane does not have to create a suction force. For example, after filling the storage space with fluid e.g. saline, intimate contact between the membrane and tissue site can be sufficient to permit diffusional fluid exchange through the membrane and tissue to collect material for analysis. In another example, the balloon may also be moved slightly axially to lightly brush the membrane against the surface, which gently sloughs the sample from the surface. This latter embodiment is preferably carried out with a hydrogel coating over the membrane since its high lubricity, low frictional coefficient characteristics allow sample collection without excessive scraping of the surface. The sample may collect in the pore openings and may not enter the spaces in the body of the polymer. In embodiments, the sample is taken simultaneously with the dilatation of a stenosis. In this case, the membrane is provided on a dilation balloon and the balloon is inflated to dilatation pressures, e.g. 8–10 atmospheres. The invention is also applicable to areas other than the vascular system, such as the lungs or gastrointestinal tract, the urinary tract, the reproductive tract, or other parts of the body; especially those that can be accessed percutaneously by a catheter or like device.

The samples collected may be analyzed by techniques that can give a physician important information in determining or monitoring treatment. For example, a bodily sample of artherosclerotic plaque, endothelial cells, or chemical messengers, can be taken from an occluded region of an artery, particularly the coronary arteries or peripheral vessels, and analyzed to determine whether an injury has occured and, also the nature of the injury. For example, the analysis can determine whether the occlusion is highly calcified, or highly cholesteric, or highly fibrotic. These types of lesions may be differentiated based on cell samples or chemical indicators such as enzymes or proteins that are precursors to, for example, proliferation. DNA and RNA samples may as well be analyzed to the same effect. Analyses may be done by visual inspection, chemical analyses or spectral analyses, and by using methods such as gel permeation chromotography, infrared spectroscopy, electrophoresis, and micro analytical techniques. For example, plaque recognition by laser excited fluorescence spectroscopy is discussed by Bertorelli et al., *JACC*, Vol. 17, No. 6, May 1991, p. 160B, which is incorporated by reference. In some cases, the type of sample may be determined by visual observation by a physician. An example is a highly calcified sample. Samples, particularly cell samples, can also be analyzed for malignancy.

This information can determine what course of treatment should be followed. For example, if the sample is highly calcified, a laser ablation treatment may be the most effective in removing the occlusion. If highly cholesteric, a cholesterol dissolving drug may be delivered to the site or systemically. If highly fibrotic, an antiproliferative drug may be delivered. Another possible treatment is gene therapy including the delivery of antisense biochemical drugs. Gene therapy is discussed, for example, in Nabel et al., *JACC*, Vol. 17, No. 6, May 1991, 189B–94B, the entire contents of which is incorporated herein by reference. For example, gene therapy can be used to introduce DNA into somatic cells to correct or prevent disorders such as atherosclerosis and restenosis caused by the malfunction of genes within the diseased individual. A drug delivery system is described in U.S. Pat. No. 5,304,121, incorporated supra. Drug delivery is also discussed in Wang U.S. Pat. No. 5,254,089, incorporated supra.

In cases where cells are obtained using the methods and devices described above, in addition to or instead of analysis, the cells may be cultured outside the body and then placed back into the patient. For example, the cells may be placed back into the patient as an autologous coating on a graft or stent. The cells may also be placed back into the body using the device described above by disposing them on or through the membrane outside the body, delivering the device to position the membrane at a desired site inside the body, then releasing the cells from the membrane by applying flushing force as discussed, for example, with respect to drug delivery in Wang U.S. Pat. No. 5,254,089 incorporated supra. The cells may also be altered, e.g. genetically, before placing them back into the body.

Another technique for collecting samples is discussed in an application filed on the same day as this application U.S. Ser. No. 08/175,791 by Sahatjian entitled "Bodily Sample Collection"; the entire contents of this application is incorporated herein by reference.

Still further embodiments are within the following claims. For example, methods and apparatus described above can be constructed and adapted for taking samples from parts of the body other than the vascular system.

What is claimed is:

1. A kit for treating a patient by collecting and treating a cell sample from a desired location in the patient, comprising:

a sampling probe in the form of an elongate catheter having a proximal portion that remains outside the body and a distal portion that can be located at the desired location, said distal portion including an expandable member that can be selectively expanded to larger diameters and contracted to smaller diameter, said expandable member including a membrane on at least a part of an outside surface of said expandable member, said membrane including openings that may receive said cell sample and which communicate with a suction device, controllable from proximal portions outside the body, for creating a suction force through said openings to draw said cell sample into said openings, an apparatus for facilitating collection and treatment of said cell sample outside the body, and a device for reintroducing said cell sample into the body.

2. A method for taking a cell sample from a desired location along a blood vessel of a patient and collecting said sample outside the body to facilitate treatment of the patient, comprising:

providing a sampling probe in the form of an elongate vascular catheter having a proximal portion that remains outside the body and a distal portion that can be located in the blood vessel during use, said distal portion including an expandable member that can be selectively expanded to larger diameter and contracted to smaller diameter, said expandable member including a membrane thereon with openings that communicate with a source of suction force controllable from the proximal portion that remains outside the body, positioning said expandable portion at a desired location within said blood vessel, taking said sample by exposing said membrane by expanding said expandable portion to place said membrane in proximity with the wall of said blood vessel so that said sample is received by said membrane, contracting said expandable portion to said smaller diameter, removing said catheter from said patient, collecting said sample outside the body, treating said cell sample, disposing the resultant treated cell sample onto a device, delivering said device on which said treated cell sample is disposed to a desired site in said blood vessel to reintroduce said treated cell sample into the body.

3. The method of claim 2, including drawing said cell sample to the surface of said membrane by suction forces.

4. The method of claim 3, comprising drawing said sample with said suction forces through said membrane of said sampling probe into a storage space.

5. The method of any one of claims 2, 3 or 4 comprising:

removing said sample by flushing force back out through said openings.

6. The method of any one of claims 2, 3 or 4 comprising:

expanding said expandable portion to contact said membrane with said vessel wall.

7. The method of any one of claims 2, 3 or 4 comprising:

moving said catheter axially while said membrane is in contact with said wall of said vessel to brush said membrane along said wall to collect said sample.

8. The method of any one of claims 2, 3 or 4 comprising:

providing a probe in the form of an angioplasty catheter having an expandable portion in the form of an inflatable balloon, said membrane being disposed over said balloon.

9. The method of claim 8 comprising:

performing angioplasty on an occluded region of said blood vessel, positioning said expandable portion at said region at said region after said angioplasty, and collecting said sample from said region.

10. A method for taking a cell sample from deep within the body of a patient and collecting said sample outside the body to facilitate treatment of the patient, comprising:

providing a sampling probe in the form of an elongate catheter having a proximal portion that remains outside the body and a distal portion that can be located within the body, said distal portion including an expandable member that can be selectively expanded to larger diameters and contracted to smaller diameter, said expandable member including a membrane on at least a part of an outside surface of said expandable member, said membrane including openings that communicate with a suction device, controllable from proximal portions outside the body, positioning said catheter within the body, taking said cell sample by expanding said expandable member to place said membrane in proximity to a desired location so that said cell sample is received by said membrane, removing said catheter from said patient, collecting said sample outside the body, treating said cell sample, disposing the resultant treated cell sample onto a device, delivering said device on which said treated cell sample is disposed to a desired site in said blood vessel to reintroduce said treated cell sample into the body.

11. The method of claim 2 or 10, wherein said device is a graft or stent.

12. The method of claim 11, wherein said treated cell sample is disposed as an autologous coating on said graft or stent.

13. The method of claim 2 or 10, wherein said device is a catheter.

14. The method of claim 13, wherein said catheter comprises an expandable member including a membrane thereon with openings that communicate with a source of suction force.

15. The method of claim 13, wherein said treated cell sample is disposed on said membrane.

16. The method of claim 15, wherein said treated cell sample is released by a flushing force back out through said openings of said membrane.

17. The method of claim 2 or 10, wherein said treating step comprises culturing said cell sample.

18. The method of claim 2 or 10, wherein said treating step comprises genetically altering said sample.

* * * * *